US006188813B1

(12) United States Patent
Dourdeville et al.

(10) Patent No.: US 6,188,813 B1
(45) Date of Patent: Feb. 13, 2001

(54) FLOW CELL, ANALYTE MEASUREMENT APPARATUS AND METHODS RELATED THERETO

(75) Inventors: Theodore A. Dourdeville, Marion; Anthony C. Gilby, Foxborough; Dennis DellaRovere, Mendon, all of MA (US)

(73) Assignee: Waters Investments Limited

( * ) Notice: Under 35 U.S.C. 154(b), the term of this patent shall be extended for 0 days.

(21) Appl. No.: 09/247,699

(22) Filed: Feb. 10, 1999

(51) Int. Cl.$^7$ ............... G02B 6/00; G01J 1/04; G01N 21/00; A23P 1/00
(52) U.S. Cl. ............ 385/12; 385/141; 250/227.11; 250/225.25; 250/573; 356/436; 425/542; 425/547
(58) Field of Search ............ 385/12, 123, 141, 385/125; 250/227.11, 227.25, 573; 356/436; 425/542, 547, 552

(56) References Cited

U.S. PATENT DOCUMENTS

| 3,867,033 | * | 2/1975 | Hasinger | 385/12 X |
|---|---|---|---|---|
| 4,045,668 | * | 8/1977 | Pitt et al. | 385/12 X |
| 4,472,022 | * | 9/1984 | Bearcroft et al. | 385/12 X |
| 4,867,559 |   | 9/1989 | Bach | 356/73 |
| 4,909,588 | * | 3/1990 | Harner et al. | 385/12 X |
| 5,153,679 |   | 10/1992 | Gilby | 356/440 |
| 5,184,192 |   | 2/1993 | Gilby et al. | 356/246 |
| 5,191,388 | * | 3/1993 | Kilham | 356/335 |
| 5,444,807 | * | 8/1995 | Liu | 385/125 |
| 5,608,517 |   | 3/1997 | Munk | 356/246 |

OTHER PUBLICATIONS

Authors: Robert D. Waterbury, et al Titled: Long pathlength absorbance spectroscopy:trace analysis of Fe(II) using a 4.5 m liquid core waveguide Journal: Analytica Chimica Acta 357 (997) 99–102.

Authors: Purnendu K. Dasgupta, Zhang Genfa, Simon K. Poruthoor, Steven Caldwell, Shen Dong Title: High–Sensitivity Gass Sensors Based on Gas–Permeable Liquid Core Waveguides and Long–Path Absorbance Detection Journal: Anal. Chem. 1998, 70, 4661–4669.

Authors: M. Osterfeld and H. Franke, C. Feger Title: Optical gas detection using metal film enhanced leakymode spectroscopy Journal: Appl. Phys. Lett, 62 (19), May 10, 1993.

Authors: Robert Altkorn, Ilia Koev and Amos Gottlieb Title: Waveguide Capillary Cell for Low–Refractive–Index Liquids Journal: Applied Spectroscopy, vol. 51, No. 10, 1997.

Authors: P. Dress and H. Franke Title: Using a Liquid–core waveguide Journal: American Institute of Physics Rev. Sci. Instrum. 68 (5), May 1997.

* cited by examiner

*Primary Examiner*—Brian Healy
(74) *Attorney, Agent, or Firm*—Brian Michaelis; Anthony J. Janiuk (57) ABSTRACT

A modular flow cell having a high optical throughput, a long optical path length and a small cross-section. The modular flow cell configuration includes remote ports or connections for liquid and light input, and liquid and light output. The flow cell includes a flow cell body having two ends, each with a respective end interface secured thereto. The flow cell is configured to form a part of a modular flow cell assembly. The flow cell body includes a channel having a through-aperture with an inner surface. A light guiding material, e.g. a transparent fluoropolymer material having a refractive index less than the refractive index of common chromatography solvents, is disposed proximate to the channel to form a light guiding through-aperture in the flow cell body. The channel is formed of materials that can provide the necessary mechanical strength and a fluid seal, and more particularly, includes materials such as polyetheretherketone (PEEK), which can develop a fluid seal at the interface between the flow cell body end and each end interface.

22 Claims, 8 Drawing Sheets

FLOW CELL, ANALYTE MEASUREMENT APPARATUS AND METHODS RELATED THERETO

FIELD OF INVENTION

The present invention relates generally to photometric devices and apparatuses for spectroscopic analysis of small absolute amounts of analyte in solution, and more particularly to a flow cell assembly using an amorphous fluoropolymer material for light conduction through the flow cell.

BACKGROUND OF THE INVENTION

Light absorption detectors for high performance liquid chromatography ("HPLC"), capillary liquid chromatography (capillary LC or "CLC"), capillary electrophoresis (CE) and capillary electrochromatography ("CEC") generally include four basic components; a light source, a means for selecting range of wavelengths, a flow cell and at least one light sensor that measures the amount of light being transmitted through the flow cell. The apparatus may be disposed with parallel optical paths as a double beam instrument. The flow cell is typically in the form of a hollow tube through which a sample to be analyzed and the light are passed. Also these four basic components are typically configured to be in a predetermined arrangement with respect to each other. With these kinds of detectors, it is known that when a sample to be analyzed passes through the flow cell, the amount of light transmitted through the flow cell decreases in accordance with Beer's law.

In conventional flow cells, light is typically passed through the flow cell in one of two fashions, along the long axis of the hollow tube or perpendicular to the long axis. In either case, i.e. when the light is parallel to the long axis or introduced perpendicular thereto, the detector or light sensor output is usually expressed in terms of absorbance, which is proportional to the sample concentration and the pathlength. Thus, the longer the pathlength, the larger the detector output signal should be for a given sample concentration. For conventional flow cells, however, the light striking the lateral wall of the flow cell is partially lost due to absorption and scattering at the wall. This lost light reduces the light energy throughput of the flowcell thereby causing an increase in the noise in the output signal of the detector.

The lateral dimension or diameter of the flow cell could be increased to reduce the fraction of light striking the lateral wall, but this increases the volume of the flow cell. Frequently, however, the quantity of the sample is limited, thus the optimum cell has a minimum volume implying a small cross-section or diameter. In addition, a larger cell volume also has the effect of spreading out or dispersing the sample peak and causing a loss in chromatographic resolution. Thus, as a practical matter the foregoing effects limit the pathlength and lateral dimension of conventional flow cells.

There is described in U.S. Pat. No. 5,608,517 a flow cell having a flow passage that is coated with a polymer having an index of refraction lower than that of common chromatography solvents, e.g. water. With such a flow cell, the light being directed into the flow cell is internally reflected or piped down the length of the flow passage. It is difficult, however, with such a flow cell to obtain consistent well adhered layers of the polymer on the inner wall of the housing for the flow cell. Thus, it is possible for the polymer layer to become detached from the housing inner wall or delaminated therefrom. This delaminating effect leads to distortion of the fluid flow channel causing distortion of the optical path and the fluid flow in the flow cell, as well as creating a condition whereby the fluid could flow between the polymer and the housing.

There also is described in U.S. Pat. No. 5,184,192, owned by the assignee of the present invention, a flow cell having an inner wall formed of an amorphous fluoropolymer having a refractive index less than the refractive index of common chromatography solvents, e.g. water. Although the flow cells described therein are capable of yielding a cell with a long pathlength, the process required for making such a flow cell, and the resultant flow cell, may not be suitable for particular applications.

Moreover, the apparatuses or systems using either of these referenced flow cells must be arranged so the flow cell is precisely located with respect to the other components constituting the apparatus or system. That is, these flow cells must be precisely located in the optical path between the light source and the light sensor or detector. The criticality of the location of known flow cell(s) is the result of the need for continual, optimal alignment, which yields greater reliability and greater analytical reproducibility. Additionally, it is generally preferred to minimize the length of the flow channel between for example the chromatography column and the flow cell, which is necessarily limited by construction and design of such apparatuses or devices. Thus, even though the above described flow cells may be capable of achieving a long path length, they are typically located with respect to other components of the detection device or apparatus in the same fashion as conventional flow cells, which do not generally optimize placement from a chromatography standpoint.

A flow cell described in U.S. Pat. No. 4,867,559 includes a cladding liquid passed through a capillary in order to coat the interior bore with a low refractive index fluorocarbon. The fluorocarbon is disclosed as being a viscous, inert, immiscible, nonwetting material, such as fluorinated oil generally available under the tradenames Fluorinert® or Krytox®. This arrangement, however, is extremely unsatisfactory in practice or use. This arrangement requires a complex fluid cladding handling mechanism, including pumps and plumbing, for delivering the cladding fluid to the capillary bore, and retrieving the excess fluid after the bore has been coated. Also, interfaces and seals must be implemented, which allow delivery of the cladding fluid to the bore while not interfering with delivery of the sample that is to be delivered to the bore subsequent to the coating by the cladding fluid. Further, the delivery and withdrawal of excess cladding fluid requires careful flow calibration, as the viscosity of the fluid and the small bore of the capillary can lead to irregular coating in the capillary. This adds considerably to the complexity and expense of the flow cell.

In addition, the cladding fluid is not bonded to the interior surface of the bore, thus it must be delivered shortly before the introduction of analyte in order to prevent settling of the cladding fluid inside the bore. Further, the cladding fluid may not fully coat the interior surface of the bore, leaving gaps in the cladding that leads to scattering of the optical signal and signal attenuation. Moreover, another problem that can result is the contamination of the sample with the cladding fluid, precluding the possibility of collection of pure fractions of the sample, which could possibly interfere with a downstream analytical technique, such as mass spectrometry.

SUMMARY OF THE INVENTION

The present invention provides a modular flow cell having a high optical throughput, a long optical path length and a small cross-section. The modular flow cell configuration includes remote ports or connections for liquid and light input, and liquid and light output. The modular flow cell can therefore be configured in a location optimized for chromatographic performance, in a chromatography apparatus or system. Novel methods are described for making the flow cell components, and for joining two materials or items together in fabrication of, for example, modular flowcell components. Such flow cells enable light to be guided axially along a sample filled tube or capillary, independent of the wall material of a transport tube. The modular flow cell of the present invention is optimally positioned relative to system components of a measuring apparatus or system and is easily installed as compared to prior art devices.

According to one aspect of the present invention the flow cell includes a flow cell body having two ends, each with a respective end interface secured thereto. The flow cell is configured to form a part of a modular flow cell assembly.

The flow cell body includes a channel having a through-aperture with an inner surface. A light guiding material, e.g. a transparent fluoropolymer material having a refractive index less than the refractive index of common chromatography solvents, is disposed proximate to the channel to form a light guiding through-aperture in the flow cell body. In a more specific embodiment, the flow cell body is included in a housing. The light guiding material in the flow cell body is, illustratively, one of a coating of a Teflon AF that is deposited onto the inner or exterior surface of the channel or is an extruded tubular member of Teflon AF that is in mechanical engagement with the channel. In any case, a hydraulic seal is established between the light guiding material and the boundary wall of the channel so the liquid sample does not bypass the through-aperture and flow along the exterior of the light guiding material on the inner surface. The channel is formed of any one of a number of materials that can provide the necessary mechanical strength and a fluid seal, and more particularly, includes materials which can develop a fluid seal at the interface between the flow cell body end and each end interface. Such materials include for example, polyetheretherketone (PEEK).

Each end interface includes an interface housing having a light transmitting passage and fluid flow passage disposed therethrough. The light transmitting passage is arranged in each end interface housing and the end interfaces are secured to the flow cell body so that one end of the light transmitting passage in each end interface is in optical communication with the through-aperture in the flow cell body. Each end of the flow cell body also is configured with an outwardly extending fluid channel that couples one end of the fluid flow passage in each end interface with the through-aperture of the flow cell body.

Each end interface includes a optical fiber as the light transmitting passage and a capillary tube, such as a quartz capillary tube, as the fluid flow passage. The interface housing in the illustrative embodiment is made of PEEK.

In a more specific aspect of the present invention the interface housing is a PEEK over-mold in which is disposed the optical fiber and the capillary tubing to effectively form an integral structure. More particularly, the molding process is performed in such a manner that the PEEK intimately engages (e.g., adhesively bonds or frictionally engages) to the outer surface of the capillary tubing and the optical fiber, thereby establishing a strong mechanical connection and a hydraulic seal between the end member housing and each of the optical fiber and the capillary tubing. Additionally, the capillary tubing and/or optical fiber can include surface artifacts interior to the over-mold to improve the mechanical bonding with the housing. The free ends of the optical fiber and the capillary tubing are configured to extend outwardly from the end interface.

The flow cell according to the invention is integrated into an analyte measurement system for analyzing a fluid sample. The system includes a sensing device, a radiation source, a flow cell assembly with the flow cell according to the present invention, and interconnections optically interconnecting the flow cell assembly to each of the radiation source and the sensing device and fluidically interconnecting the flow cell with the fluid system(s). In such a system the flow cell assembly is capable of being located physically independent of, and thus isolatable (e.g., electrically isolated), from each of the radiation source and the sensing device. Thus, and in contrast to prior art devices, the flow cell assembly of the present invention does not have to be precisely located immediately adjacent to other system optical components to maintain a given optical configuration in order to reliably and reproducibly provide a signal output. In addition, because the flow cell assembly can be physically and electrically independent it can be configured modularly for easy replacement in the field.

The modularized flow cell assembly includes the flow cell as hereinabove described, mounted in a frame including optical fiber interconnections and capillary tubing interconnections. The fiber optic interconnections couple the free ends of the optical fiber extending outwardly from each end interface with optical ports provided in each of the radiation source and the sensing device. The capillary tubing interconnections are effected by any of a number of techniques known to those skilled in the art for fluidically interconnecting the free ends of the capillary tubing extending outwardly from the end interfaces to a fluid source and fluid sink, respectively.

The radiation source in the assembly incorporating the flow cell according to the invention, is a source of electromagnetic radiation that provides output in a predetermined fashion across a wide spectral range or a narrow band. In an illustrative embodiment, the radiation source is a light source including a deuterium lamp having spectral emissions encompassing the range from about 190 nm to about 800 nm.

The sensing device in the assembly according to the invention comprises a diffraction grating and photodiode array for sensing the light transmission through the fluid sample being analyzed, and for providing an output representative of that transmission.

In use, the fluid sample from the sample source (e.g., chromatographic column) flows through the flow passage or capillary tubing in one end interface and into the through-aperture in the flow cell body formed by the inner surface of the light guiding material. Fluid sample flows from the through-aperture, out through the flow passage or capillary tubing of the second end interface to a waste collection means or other downstream process. In this way, a static or flowing fluid sample is located in the through-aperture for analysis purposes. One end of the light transmitting passage or optical fiber extending out of one end interface is optically interconnected to the radiation source so the radiation or light therefrom passes through the light transmitting passage to the through-aperture in the flow cell body member. As described hereinabove this light is channeled by the light guiding material in the body so that the light traverses the cell substantially parallel to the long axis of the through-aperture. Correspondingly, the other end of the light transmitting passage or optical fiber extending out of the second end interface is optically interconnected to the sensing device so that the radiation or light that has traversed the cell exits the flow cell body through-aperture and passes into the sensing device.

Features of the invention include provision of a modular flow cell that is easily installed as a module in the context of system components, such as a radiation source and a sensing device. The flow cell and apparatus or system in which the flow cell is located is capable of being remoted a short distance from either the light source and light sensor or detector, as well as being electrically isolated therefrom. Such flow cells and measuring systems according to the invention are less costly and less difficult to manufacture in comparison to prior art devices. In addition, manufacturing and methods of use of the described flow cells and related apparatuses and systems are significantly simplified. The end interfaces are formed by a low cost, easily implemented over-molding process. The resultant flow cell is of a rugged, durable construction. The manner of construction allows one to easily manufacture flow cells having different pathlengths.

BRIEF DESCRIPTION OF THE DRAWING

These and other features and advantages of the present invention will become more apparent from the following detailed description taken in conjunction with the accompanying drawings wherein like reference characters denote corresponding parts throughout the several views, and wherein.

DETAILED DESCRIPTION

Referring now to FIGS. 1–4 a flow cell 10 according to the present invention includes a flow cell body 20, two end interfaces 40 and two clamping members or flanges 12 that hold the two end interfaces 40 in fixed mechanical engagement with the cell body 20. As shown most clearly in FIG. 4, the cell body 20 includes a housing 24, which in this illustrative embodiment is made of stainless steel. A first interior material or layer 26 is disposed on the inner surface of a channel 25 within the housing. An inner light guiding material 28 is disposed within the first interior material or layer 26. The housing 24, first interior layer 26 and the inner light guiding material 28 are configured to form a through-aperture 30 that passes along the long axis of the cell body 20. As is known in the art, in operation a flowing or static fluid sample to be analyzed is disposed in the through-aperture 30 of the flow cell 10.

Figure 4:
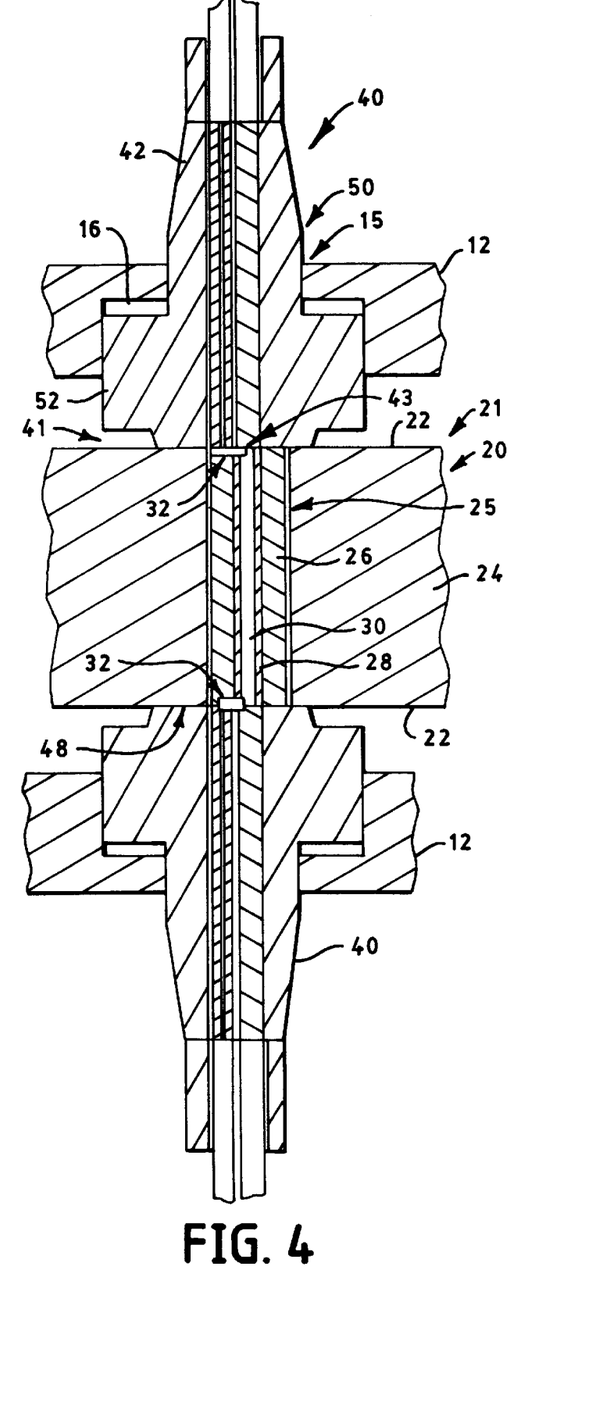
FIG. 4 is a cross-sectional view of a part of the flow cell of FIG. 1.

In the illustrative embodiment, the first interior material or layer 26 is a tubular member of PEEK that is drawn into the channel 25 of the housing 24 so that the first interior layer fixedly engages the inner surface of the housing channel. The PEEK tube has an outer diameter of approximately 0.062 inches (or larger) and an inner diameter of approximately 0.020 inches. The corresponding inner diameter of the housing channel 25 is slightly smaller than the outer diameter of the PEEK tube to facilitate fixed engagement. Although PEEK is described illustratively, other chemically inert material(s) with similar sealing properties could be used, such as perfluoroamines (PFA).

The light guiding material 28 in this illustrative embodiment has a refractive index less than the refractive index of the liquid comprising the fluid sample within the cell body through aperture 30 over a desired spectral range (e.g., from UV through visible). In this illustrative embodiment the light guiding material 28 is an amorphous fluoropolymer such as amorphous copolymers of perfluoro-2,2-dimethyl-1,3-dioxole with tetrafluoroethylene, sold under the tradename Teflon® AF 1600 or 2400. Teflon® AF 1600 fluoropolymer has a refractive index of 1.31 at the sodium D line and Teflon® AF 2400 fluoropolymer an index of 1.29. As comparison, the refractive index of water at this wavelength is 1.333. At ultraviolet wavelengths, the indices of both water and the fluoropolymers increase, but the index of the water remains higher.

The light guiding material 28 is disposed on and along the inner surface of the first interior layer or PEEK tube 26 using any one of a number of techniques. The inner wall or surface formed by the light guiding material 28, and correspondingly the wall of cell body through-aperture 30, is preferably smooth or mirror like to enhance the optical properties thereof. In this way, light or radiation directed into one end of the through-aperture 30 is reflected down and along the length of the through-aperture, or in other words it is piped. With such a configuration the light is piped down the through-aperture 30 without substantial loss of light through the light guiding material 28.

In one embodiment, the light guiding material 28 is an extruded tube of light guiding material, such as tubular extruded Teflon AF, having an outer diameter selected to mechanically engage the inner surface of the first interior layer 26. In the illustrative embodiment, as indicated above, the first interior layer 26 is a tube of PEEK having an inner diameter of approximately 0.019 inches. The extruded tube comprising the light guiding material 28 has an outer diameter of about 0.020, and frictionally engages the inner diameter of the PEEK tube comprising the first interior layer 26. The thickness of the light guiding material 28 is established so it is not distorted significantly as it is drawn into and down through the aperture in the PEEK tube. Accordingly, substantially all of the evanescent wave associated with internally reflected light is prevented from reaching the flow cell housing 20. For example, the wall thickness of the extruded tubular Teflon AF member comprising the light guiding material 28 is about 0.010 inches.

In this illustrative embodiment, Teflon AF tubing is drawn into the first interior layer 26 of PEEK. Any excess Teflon AF tubing is cleaved, and optimally the face of the cell body structure (housing, PEEK tubing and Teflon AF tubing) is lapped to provide a smooth surface.

In an alternative embodiment, the light guiding material 28 is formed by coating or depositing one or more layers of the amorphous fluoropolymer on the inner surface of the first interior layer 26. In this illustrative embodiment the first interior layer 26 is PTFE, a sintered fluorocarbon. The Teflon AF fluoropolymer is then coated onto the inside surface of the first interior layer 26 by flowing a solution of the amorphous fluoropolymer in a solvent, such as the fluorosilane sold under the tradename Fluorinert® FC-71, to leave a film of solution on the inner surface. The solvent comprising the film is slowly evaporated which can occur at reduced pressure, and/or subject to mild warming, to speed the process. Fluorosilane solvents such as Fluorinert® solvents are suitable because they are capable of maintaining concentrations of Teflon AF in solution, and they do not leave any residue upon evaporation. The foregoing coating and evaporative disposition process is repeated as many times as is necessary to achieve the desired thickness for the light guiding material 28. After reaching the desired thickness, the flow cell body 20 is baked at a temperature above the glass transition temperature of the amorphous fluoropolymer (which is 240° C. for the Teflon® AF 2400 fluoropolymer). This baking anneals the fluoropolymer to produce a smooth and transparent film that is bonded to the inner surface of first interior layer 26. Preferably, the thickness of the light guiding material 28 formed by the coating process is at least the thinckness of several wavelengths of the transmitted light. This prevents a significant portion of the evanescent wave associated with internally reflected light from reaching the flow cell housing, where light would be lost by refraction, scattering or absorption.

After the first interior layer 26 and the light guiding material 28 are disposed and secured within the housing 24, opposing end surfaces 22 are lapped so that the end surfaces 22 are substantially parallel to each other and perpendicular to the long axis of the through-aperture 30. Additionally, the end surfaces 22 are polished to establish a mating surface capable of sealing against fluid pressure at the boundary with each end interface 40.

Figure 5A:
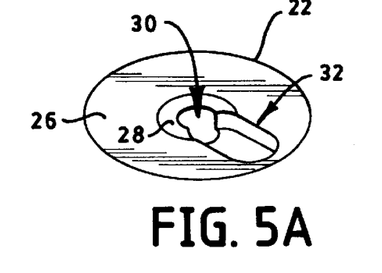
FIG. 5A is a perspective view of a portion of the flow cell body about a fluid channel (of exagerated depth) according to the present invention.

As more clearly shown in FIG. 5A, each end surface 22 is machined in the area of the first interior layer 26 and the light guiding material 28 to include a radially extending depression or end channel 32. The end channel 32 extends radially a sufficient distance so the interior passage of the capillary tube 46 in each end interface 40 is in fluid communication with the body member through-aperture 30 as shown illustratively in FIG. 4. Additionally, the width, depth and geometric arrangement of the end channel(s) 32 are established to provide an adequate cross-section for purposes of fluid flow. It will be appreciated that the fluid channel 32 can be formed using any of a number of techniques known to those skilled in the art, such as laser ablation, mechanical machining, or the like. In an illustrative embodiment, the radially extending portion of the channel 32 is configured to have vertically extending side walls and an arcuate bottom with a width of about 0.003 inches and a minimum depth of about 0.002 inches, however alternative configurations can be implemented.

Referring back to FIGS. 1–4, and 5B, and as indicated above, the flow cell 10 also includes two end interfaces 40, each including an interface housing 42, a light transmitting member and a fluid conducting member or transport tube. More particularly, the light transmitting member is an optical fiber 44 and the fluid conducting member is a capillary tube 46, for example a quartz capillary tube.

Figure 5B:
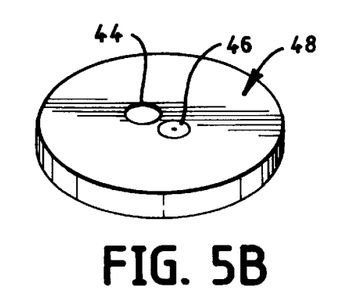
FIG. 5B is a perspective view of a flow cell end interface according to the present invention.

The optical fiber 44 and the capillary tube 46 are each disposed within the interface housing 42 and secured thereto. The optical fiber 44 and the capillary tube 46 are disposed in a manner which forms a hydraulic seal or pressure boundary between these components and the interface housing 42 so the fluid sample within the flow cell body through-aperture 30 does not leak out. The particulars regarding the method for securing the optical fiber 44 and the capillary tube 46 to the interface housing 42 are discussed hereinafter.

As shown most clearly in FIG. 4, the optical fiber 44 is disposed within the interface housing 42 so one end 43 of the optical fiber 44 is optically interconnected to the flow cell body through-aperture 30, when the end interface 40 is secured to the flow cell body. The optical fiber 44 is sized so it extends at least across the cross-sectional area of the cell body through-aperture 30. Correspondingly, the capillary tube 46 is disposed within the end interface housing 42 so the fluid passage of the capillary tube 46 communicates with the end channel 32 in the cell body 20, when the end interface 40 is secured to the cell body. Although FIG. 4 shows the end channel 32 in each end surface 22 of the cell body 20 as being disposed on the same side of the cell body, there is no requirement that the radial orientation of the fluid flow paths, i.e. end channels 32, are the same.

Figures 1, 2, 3:
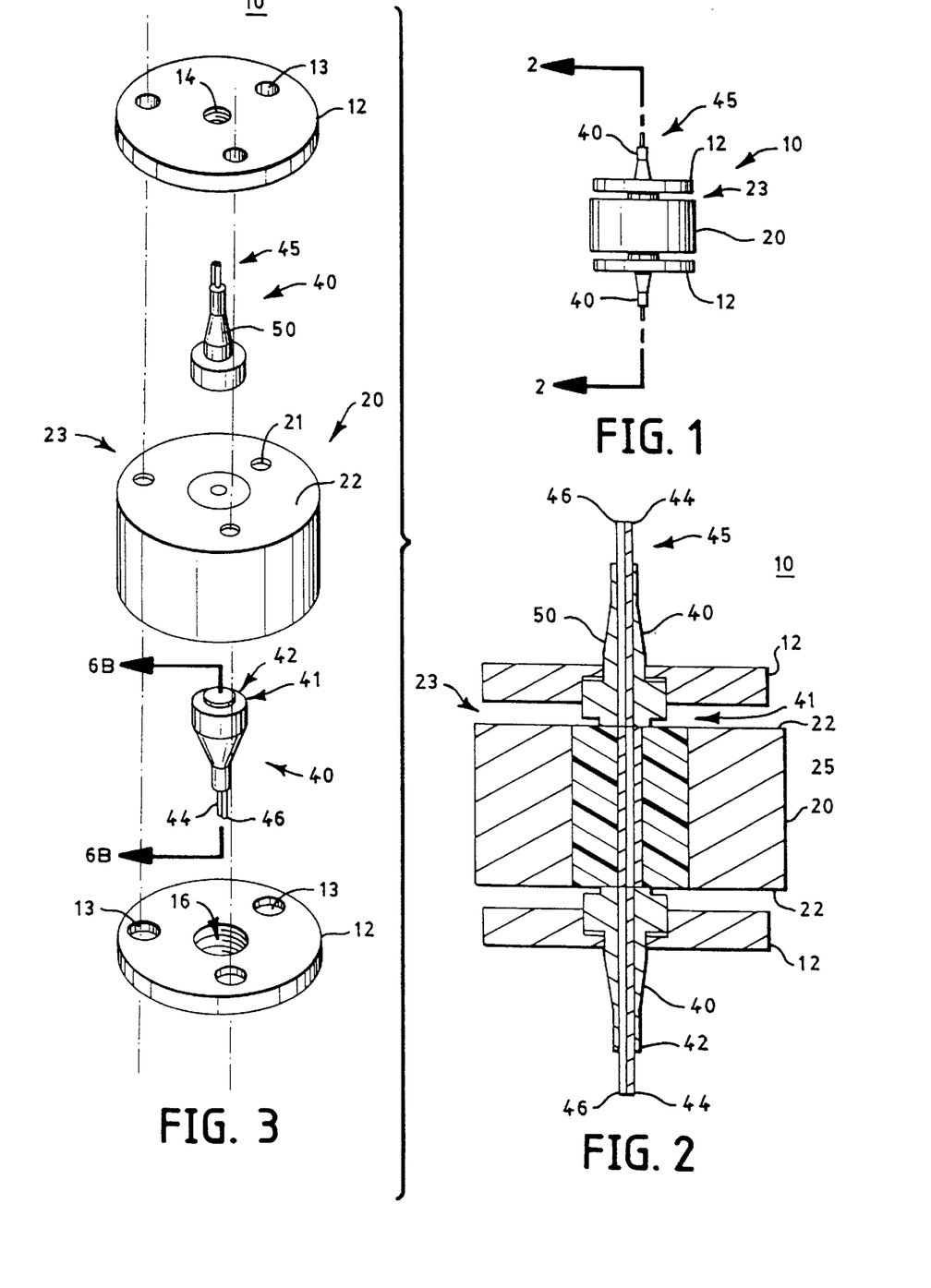
FIG. 1 is a side view of a flow cell body according to the present invention.
FIG. 2 is a cross-sectional view of a flow cell along section line 2—2 of FIG. 1.
FIG. 3 is an exploded perspective view of the flow cell of FIG. 1.
Figure 7:
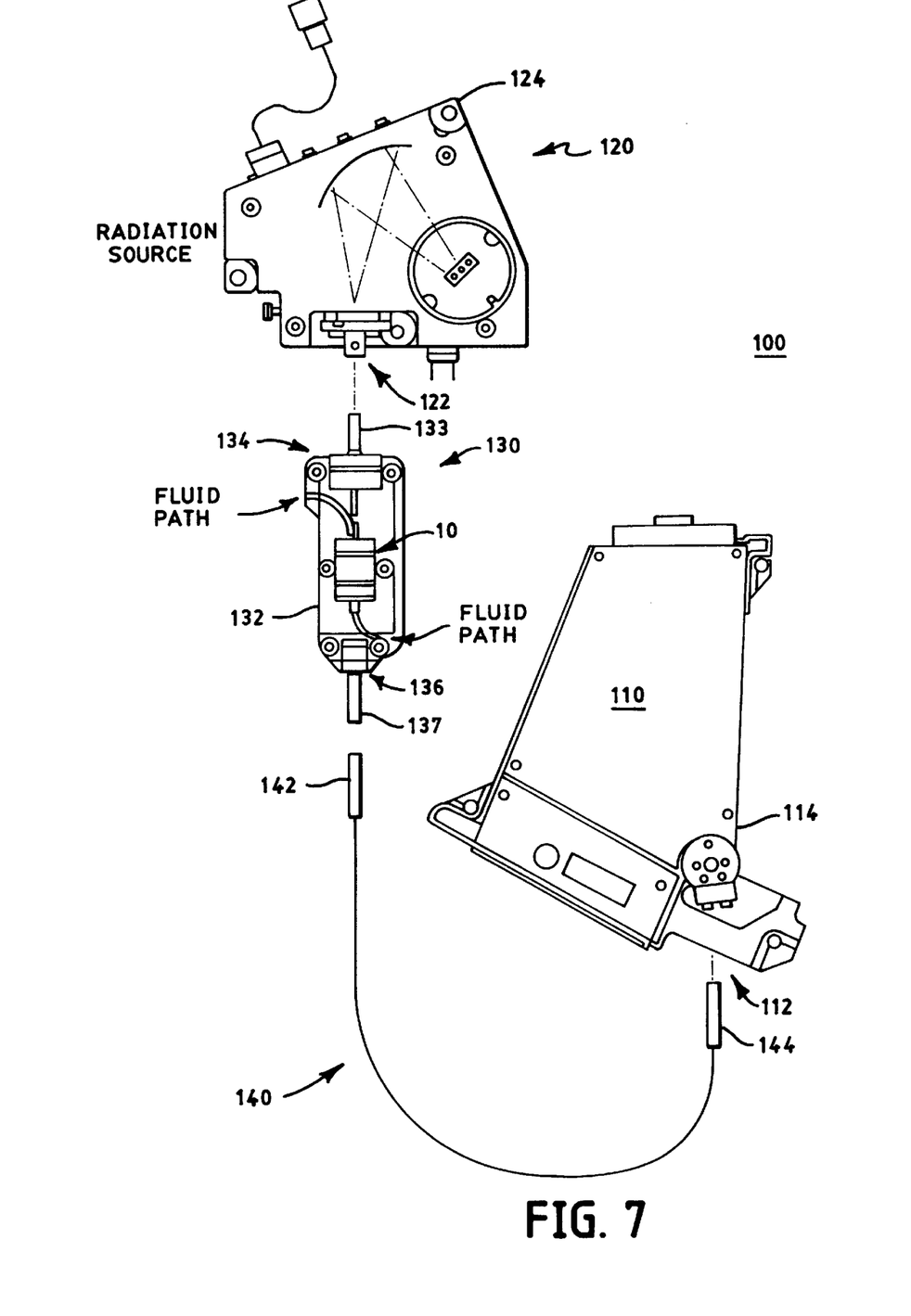
FIG. 7 is an exploded view of a detector portion of an analysis system with a modular flow cell, according to the present invention.

In use, the optical fiber 44 of one end interface 40 is optically interconnected to a radiation or light source and the optical fiber 44 of the other end interface is optically interconnected to a sensing device. Similarly, the capillary tube 46 of one end interface is fluidically interconnected to the sample source and the capillary tube of the other end interface is fluidically interconnected to a waste line or other downstream process. As such, and as shown in FIGS. 1–3, portions 45 of the optical fiber 44 and the capillary tube 46 extend outwardly from the end interface housing(s) 42 so these portions, the free ends, can be respectively optically and fluidically interconnected in the described fashion. The foregoing arrangement is illustrated in FIG. 7 and described in greater detail hereinafter.

In the illustrative embodiment the end interface housing 42 is molded from PEEK. A selected length of optical fiber and the capillary tubing is disposed within the mold to form an integral structure via the molding process. As described hereinafter, the molding process is conducted to capture the outside surfaces of the optical fiber and the capillary tube within the PEEK forming a mechanical interconnection, and forming a hydraulic seal therebetween.

Figure 6A:
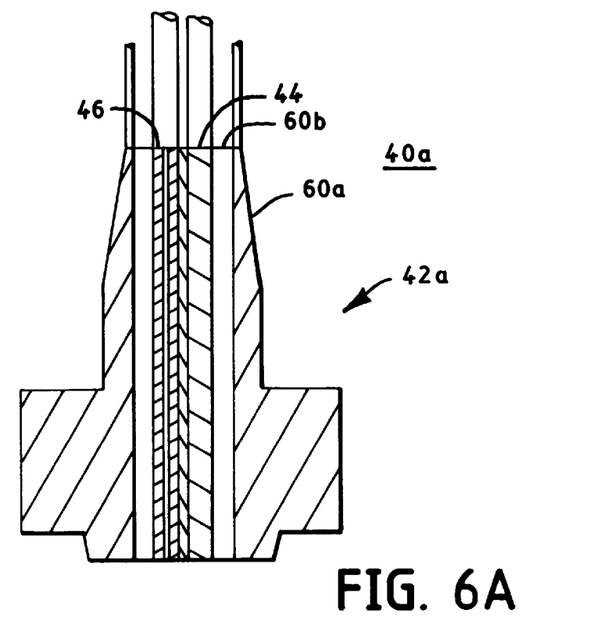
FIG. 6A is a cross-sectional view of an alternative embodiment of the end interface of the flow cell according to the present invention.

Referring also to FIG. 6A, it is within the scope of the present invention for the end interfaces 40 to include a multi-element construct type of housing 42a. For this embodiment, the multi-element housing 42a includes, for example, an outer member 60a of one material such as stainless steel and an inner member 60b of PEEK. The optical fiber 44 and the capillary tube 46 are disposed in the housing inner member 60b. Additionally, in this embodiment the PEEK comprising the housing inner member 60b is bonded to the housing outer member 60a as well as to each of the optical fiber 44 and capillary tube 46. Thus these components are mechanically secured to each other and form a hydraulic seal. It will be appreciated that the housing outer member can be any of various materials, such as curable resins or melt processable resins.

A mating end 41 of the interface housing 42 is shown in the illustrative embodiment of FIGS. 1–4 as having a raised face type of flanged surface, and the corresponding end 23 of the flow cell body 20 is shown as being a flat faced type of flanged surface. It is within the scope of the present invention, however, for the corresponding ends 23,41 of the cell body 20 and the end interface 40 to present either of a raised face or flat face type surfaces.

Figure 6B:
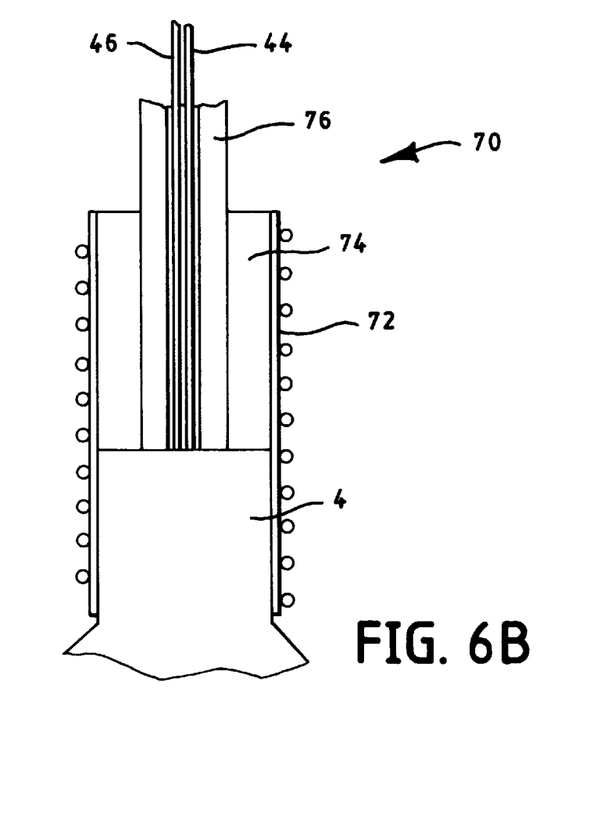
FIG. 6B is a partial cross sectional view of a strain relief implementation for an end interface of taken along a line 6B—6B FIG. 3.

In an illustrative embodiment with reference to FIG. 6B, each end interface 20 can be configured with a strain relief means 70 to protect or minimize the potential for structural failure of the optical fiber 44 and capillary tube 46 at or about the outside surface of the end interface housing 42. The strain relief means 70 includes a PTFE shrink tubing sleeve 72, an outer ethylenetetrafluoroethylene (ETFE) sleeve 74 and an inner ETFE sleeve 76. The sleeves are disposed in this order about a portion of the optical fiber 44 and capillary tube 46 extending from the end interface housing 42. Further, the PTFE shrink-tubing sleeve 72 extends along the outside surface of the end interface housing 42 so the strain relief means 70 is secured in place. Alternatively, the strain relief means 70 can include a coil spring disposed about the PTFE shrink-tubing sleeve 72.

Referring again to FIGS. 1–4, and as indicated above, the flow cell 10 also includes two clamping rings 12, that secure the end interfaces 40 to the cell body 20 so the optical fiber 44 and the capillary tube 46 are in a fixed and predetermined relationship with respect to the end channel 32 and the through-aperture 30. Each clamping ring 12 is a disc shaped member, including an aperture 14 and a depressed region 16 centered about the aperture, that is disposed about an end interface 40. When assembled, a barrel 50 of the end interface 40 is passed through the aperture 14 and a ferrule 52 of the end interface 40 is received in part within the depressed region 16. Each clamping ring is constructed from a material appropriate for the mechanical loads and environmental conditions of the intended application, including materials such as stainless steel, aluminum, or the like. The aperture 14 is dimensioned to fit snugly about the barrel 50 effecting an interference fit. Although not shown, one or more dowel pins or other alignment means can be used to effect optical and fluidic alignment between the end interfaces 40 and the flow cell body 20.

In the illustrative embodiment, the depressed region 16 has a circular vertically-extending side wall and a flat bottom to correspond with the circular geometry of the end interface ferrule 52. It is within the scope of the present invention for the end interface ferrule 52 and the depressed region 16 of each flange 12 to have any of a number of complementary geometric shapes such as rectilinear, polygonal or triangular.

As shown in FIG. 3, each of the clamping rings 12 and the cell body include a plurality of screw holes 13, 21. The screw holes 13,21 are arranged respectively in each ring 12 and the cell body about a common axis so the holes line up when the end interfaces 40 are being secured to the cell body. In the illustrative embodiment, the rings 12 secure the end interfaces 40 to, and in alignment with, the cell body 20 by means of internal threads (not shown) in the flow cell body screw holes. The screws pass through the holes 13, 21 provided in each of the rings 12 and attach the clamping rings to the flow cell body 20 via the threads. It is within the scope of the present invention, however, for the end interfaces 40 to be secured to the ends 22 of the cell body 20 using any of an number of techniques available including, other types of hardware (e.g. nuts and bolts), and adhesives securing the cell body and end interfaces 40 together, or the like. Similarly, it should be appreciated that wave washers or the like could be used to distribute the load in attaching the clamping rings to the flow cell body.

The flow cell 10 according to the invention has a number of beneficial effects. In one aspect, the cell body 20 can be easily made to have long or short pathlengths by introduction of cell body lengths as a function of the application,, without changing focussing optics. The flow cell can be positioned so it is electrically isolated from the radiation source and the sensing device so that the application of high voltages in some measurement techniques can be easily accomplished.

As in FIG. 7, an analyte measurement apparatus system 100 as would be employed in a liquid chromatography device, is configured including a sensing device 110, a radiation source 120, and a flow cell subassembly 130 including the flow cell 10 according to the present invention. Means for optically interconnecting the flow cell assembly to each of the radiation source and the sensing device are provided, in the form of sheathed fiber optic and fluid paths (reference should be made to FIGS. 1–6 and related discussions for any components or features not shown in detail in FIG. 7). In an illustrative embodiment, the modular flow cell subassembly 130 is optically interconnected to the sensing device 110 by a optical fiber 140 and to the radiation source 120 via an optical output port 122 provided in the housing 124 of the radiation source. In such a system the flow cell subassembly 130 provides a modularized flow cell subassembly that can be easily replaced in the field.

The flow cell subassembly 130 includes the flow cell as herein above described, mounted in a frame 132. The frame includes optical fiber coupling means and capillary tubing coupling means. The optical fiber coupling means is configured to couple with the free end of the optical fiber 44 extending outwardly of each end interface 40 and the optical interconnections to the radiation source and sensing device respectively. In the embodiment illustrated in FIG. 7, the free end of the optical fiber 44 of one end interface 40 is optically interconnected to a ferrule-type coupling 134 (such as an SMA connector known in the art), and the free end of the optical fiber of the other end interface is optically interconnected to a second ferrule-type coupling 136, where each of the couplings 134, 136 are secured to the frame 132. An end 133 of the first coupling 134 is configured to mate with the optical port 122 provided in the radiation source 120 and an end 137 of the second coupling 136 is configured to mate with an optical coupler provided at one end 142 of the system optical fiber 140. The other end 144 of the system optical fiber 140 is configured to mate with an optical port 112 provided in a housing 114 of the sensing device. Similarly, capillary tubing fluidic couplings are provided which can be any of a number of couplings known to those skilled in the art for fluidically interconnecting the free end of the capillary tubing extending outwardly from each end interface to one of the inlet tubing from the sample source and the waste tubing to the waste collection point.

The radiation source 120 in the illustrative system is any one of a number of sources of radiation for spectrographic analysis of a flowing or static fluid sample. For example, the radiation source 120 could be a light source including a deuterium lamp having spectral emissions encompassing the range of from about 190 nm to about 800 nm.

Likewise, the sensing device 110 can be any one of a number of devices known in the art for sensing the light transmissions through the fluid sample being analyzed. The sensing device 110 in the illustrative system may be an absorption type of detector that is configured to sense the amount of light absorbed by the analyte in solution in the fluid sample. Such a detector typically includes a photodiode array (PDA), such as a Waters 996 PDA, for sensing light in a predetermined spectral range, typically at least a range that includes the spectral emissions of the radiation source 120.

As noted above, each end interface 40 in the illustrative embodiment is a PEEK overmold, where the PEEK material comprises the end interface housing 42 and the optical fiber 44 and the capillary tube 46 are fixedly disposed therein. As also noted above, the molding process is performed so the PEEK captures the optical fiber 44 and the capillary tube 46 and thereby forms a mechanical bond and hydraulic seal therebetween.

Figure 8:
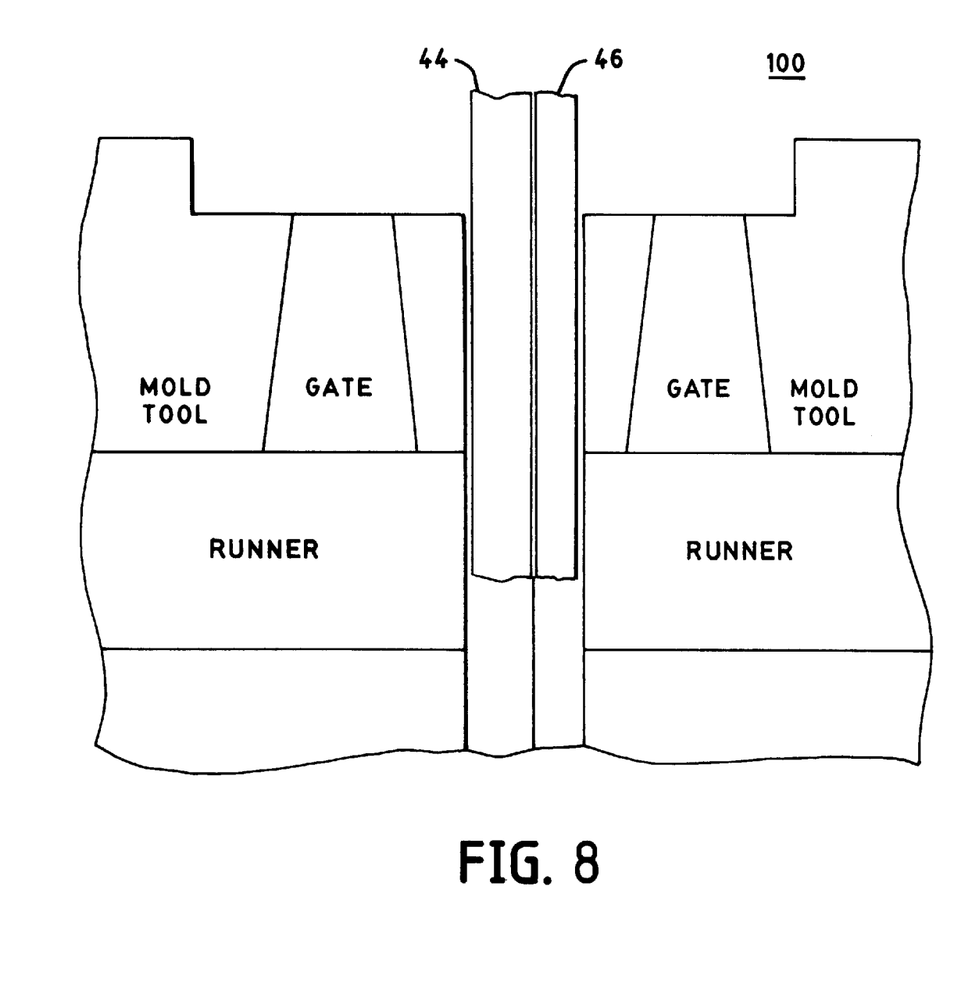
FIG. 8 is a cross sectional side view of a mold/tool for forming an end interface of the flow cell of the present invention.
Figure 9:
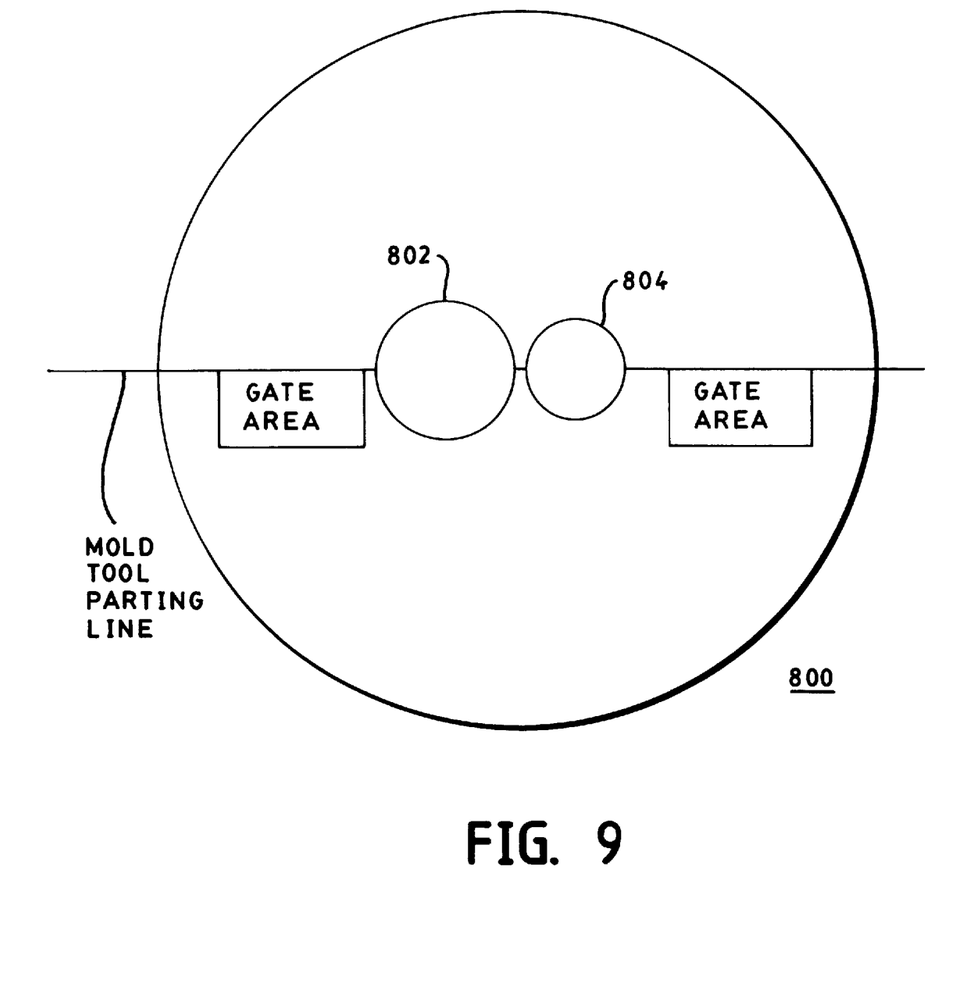
FIG. 9 is an end view of the mold/tool of FIG. 7.

Referring now to FIGS. 8–9, a process for adhesively bonding PEEK in forming the flow cell according to the invention involves a mold/tool 800 for making a molded end interface 40 according to the present invention. An optical fiber 44 and capillary tubing 46 having, for example, a length of about 12–16 inches, is located in the mold/tool 800 so a portion of each extends out of end passages 802, 804 provided in each end of the mold/tool 800.

The PEEK material is heated to a sufficient temperature to allow injection molding to occur. The liquid PEEK when so heated is further characterized by its ability to wet out the surfaces of many materials extremely well, with shallow contact angles. Such materials include materials that are solid in the temperature ranges in which PEEK is so heated and includes for example, metals such as steel of all types, aluminum and titanium and non-metallic materials such as quartz, fused silica and polymide coated quartz fibers.

After molding the excess length of the optical fiber 44 and capillary tubing 46 that is extending from the mating end 41 of each end interface 40 is cleaved close to the exposed surface of the mating end. For example, these ends of the tubing and cable are cut off by means of a thin, bonded-diamond cut-off wheel, where the plane of the cut-off wheel is parallel to the end plane of the raised-face surface of the end member. The end interface mating end 41 is then machined, surface ground, lapped and/or polished as required to provide a mating surface having the desired mating features. Additionally, the mating is polished and/or lapped so the exposed end of the optical fiber 44 has the desired optical transmissivity.

The above process yields a finished assembly that provides a smooth surface to the flow cell body 20 so there should be no observable cavities or unflushed volumes that could holdup analyte material causing carryover from one measurement interval to the next. In addition, and as noted above the PEEK material creates a hydraulic seal so the flow cell when assembled can withstand significant operating pressures.

Figure 10:
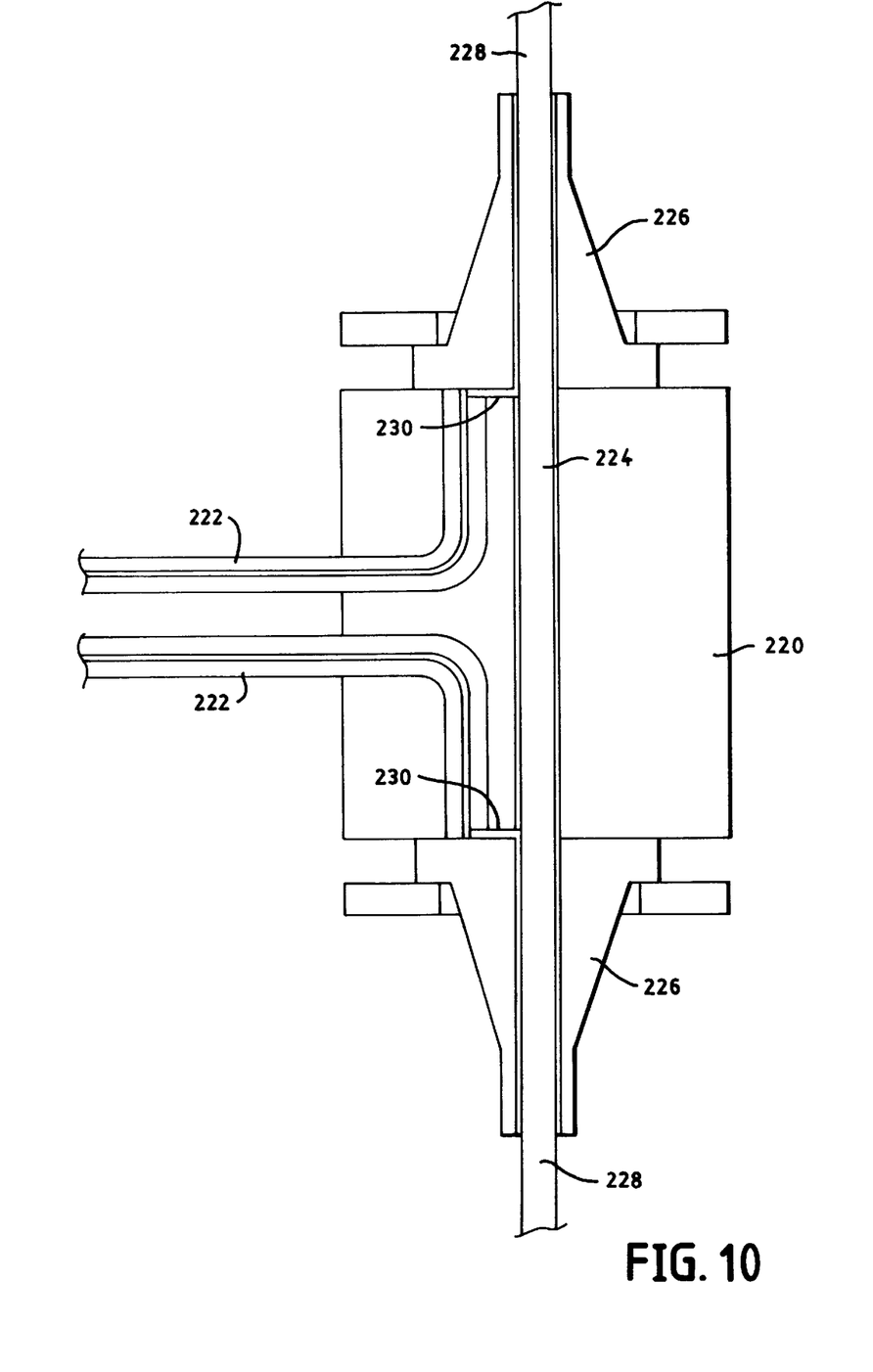
FIG. 10 is a side section view of an alternative embodiment of an improved flow cell according to the invention.

An alternative embodiment of an improved flow cell according to the invention is illustrated in FIG. 10. It should be appreciated that a cell body 220 can be configured to include fluidic channels 222 for the entry of fluid into and exit of fluid from the cell chamber 224. The chamber 224 includes a light guiding member or material as described herein with respect to the embodiment(s) of FIGS. 1–4. In the embodiment of FIG. 10, the end interfaces 226 are configured to include light transmitting members 228, in the form of respective optical fibers, engaged in the end interfaces substantially as described hereinbefore. An internal fluid channel 230 disposed in extreme ends of the cell body 220 facilitates fluid communication between the fluidic channels 222 and respective ends of the chamber 224.

Figure 11:
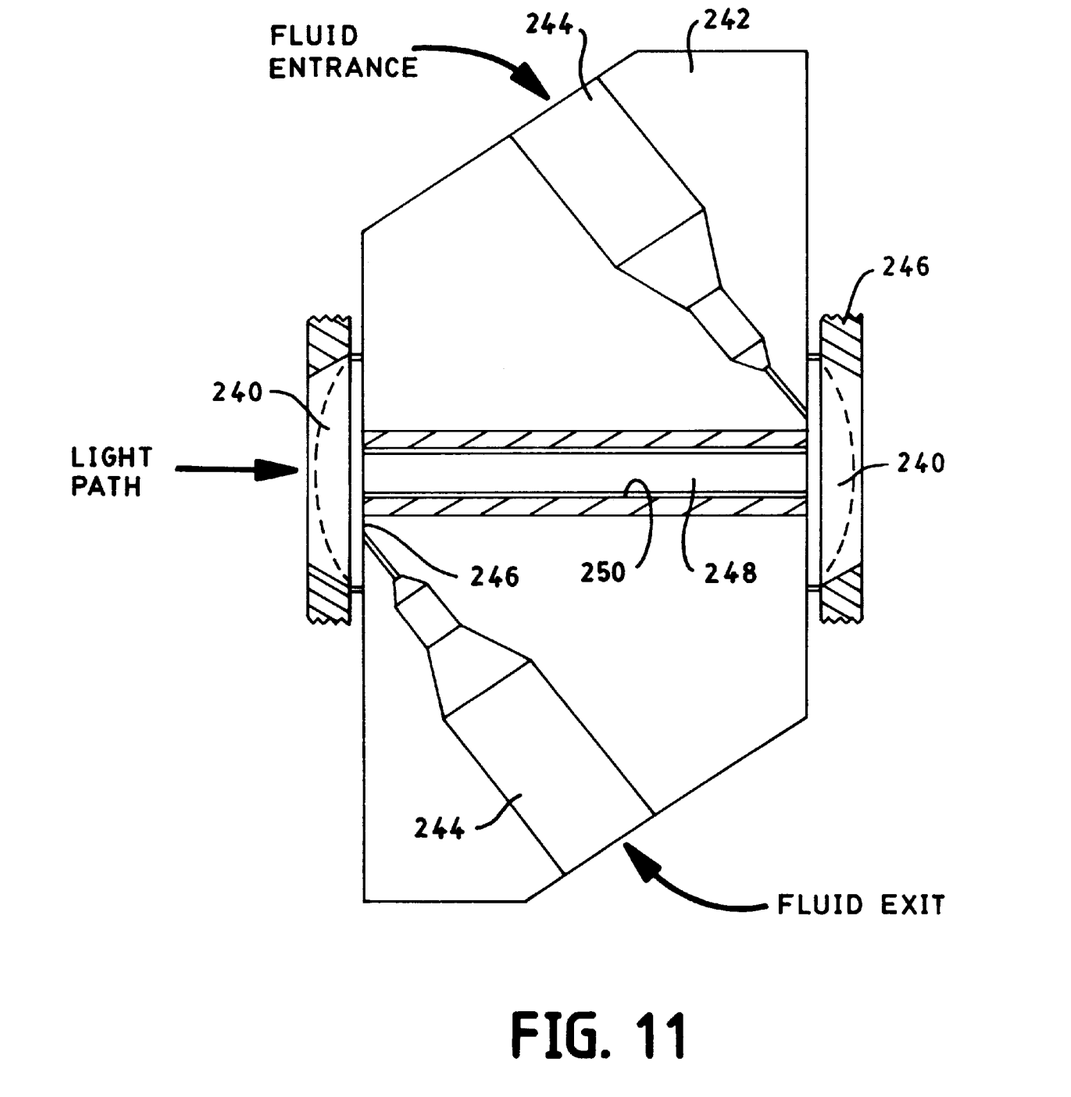
FIG. 11 is a side section view of still another alternative embodiment of an improved flow cell according to the invention.

In a still further alternative embodiment illustrated in FIG. 11, alternative light transmitting members 240 are configured for implementation at the end interfaces of the cell body 242. In this illustrative embodiment fluid channels 244 are integrated with the cell body 242. The light transmitting members 240 are implemented as quartz windows which can be fastened to the cell body 242 in any of various manners, including the use of clamping members or flanges as described hereinbefore. Cross connecting fluid channels 246 provide for fluid communication between the fluid channels 244 and the chamber 248. In such an implementation, conventional optical elements, such as lenses and/or mirrors, are used to convey light toward and away from the cell. In a further alternative implementation, the light guiding member or material, e.g. Teflon AF, is disposed external to the channel which is implemented as a fused silica tube 250.

Although the light transmitting members 240 are implemented as quartz windows in the embodiment of FIG. 11, it should be appreciated that other materials that are transparent within a wavelength of interest can be implemented as windows, rather than quartz.

Although the foregoing process describes forming the end member from PEEK that includes no fillers, it is within the scope of the present invention for fillers such as glass can be incorporated into the PEEK housing. In particular, the PEEK can include fillers that have beneficial effects for dealing with dimensional stability, shrinkage stresses and the like.

Although the foregoing describes a method of forming an end interface for a flow cell using PEEK to concurrently form a mechanical bond between the optical fiber and capillary tubing as well as form an hydraulic seal there between so the so formed end member can withstand an operating pressure, this is not a limitation of the present invention. It is within the scope of the present invention for materials other than PEEK to be used to form any of a number of standard connectors for use with optical fibers and/or quartz capillary tubing, including materials such as polyphenolenesulfide (PPS).

It should be noted that aspects of the described process (es), apart from the specific molds can be used to adhere PEEK to any of a number of materials including coated or un-coated quartz fibers and generally for forming a mechanical bond and/or hydraulic seal between one or more items by using PEEK.

Although the flow cell of the present invention is described in connection with its use in a liquid absorption detector system such as those used in high performance liquid chromatography (HPLC), capillary liquid chromatography (capillary LC), and capillary electrophoresis (CE). However, it is within the scope of the present invention for a flow cell having the same basic construction as herein described to be used for fluorescence or Raman spectroscopy or colorimetry, with flowing or static samples.

Although the illustrative embodiment herein includes a lamp, a flow cell, optics (i.e. diffraction grating) and detector, in that order, it should be appreciated that the flow cell according to the invention can be implemented in alternative configurations, for example, wherein the diffraction grating is disposed between the light source and flow cell, or wherein no diffraction grating is included and other optics (e.g. filters) are used to focus light on the detector(s).

Similarly, it should be appreciated that a photo diode array or a single photodiode can be implemented with the configuration, and/or a laser can be implemented as a light source providing a directed beam eliminating the need for optics such as the diffraction grating or filter(s).

Although the invention has been shown and described with respect to illustrative embodiments thereof, it will be appreciated that the foregoing and various other changes, omissions and additions in the form and detail thereof may be made without departing from the spirit or scope of the invention as represented by the following claims.

What is claimed is:

1. A flow cell for containing a fluid sample and exposing the fluid sample to radiation for analysis, the flow cell comprising:
    a flow cell body having a through-aperture with an inner surface, and having a first end and a second end, said flow cell body having a plastic composition allowing said flow cell body to be molded around a light guiding member;
    a light guiding member fixed to said inner surface of said flow cell body by molding and having a wetted surface defining a chamber for receiving one or more fluids, said wetted surface comprised of a amorphous fluoropolymer having a refractive index less than the refractive index of said fluid sample to direct light impinging on said wetted surface to reflect into said fluid sample;
    a first end interface disposed proximate to said end of said flow cell body and a second end interface disposed proximate to said second end of said flow cell body, each of said first and second end interface comprising a light transmitting member; and
    an inlet and an outlet fluid transmitting member disposed in one of said flow cell body and light guiding member or said first or second end interface.

2. The flow cell of claim 1 further including a first end clamping member and a second end clamping member corresponding respectively to said first end interface and said second end interface, and fastening each of said first end interface and said second end interface to and in alignment with said flow cell body first end and second end respectively.

3. The flow cell of claim 2 wherein each of said first end clamping member and said second end clamping member include holes for receiving fasteners to mechanically fasten said first end interface and said second end interface to said flow cell body.

4. The flow cell of claim 1 further including at least one internal channel configured for fluid communication between said chamber and a respective one of said inlet and outlet fluid transmitting members.

5. The flow cell of claim 1 wherein said flow cell body is made from polyetheretherketone.

6. The flow cell of claim 1 wherein said light guiding member is a tubular member of an amorphous copolymer of perfluoro-2,2-dimethyl-1,3 dioxole and tetrafluoroethylene.

7. The flow cell of claim 1 wherein said flow cell body with said light guiding member disposed proximate thereto is disposed in a housing.

8. The flow cell of claim 1 wherein said light transmitting member is an optical fiber.

9. The flow cell of claim 1 wherein said fluid transmitting member is a capillary tube.

10. The flow cell of claim 1 wherein said interface housing is a polyetheretherketone overmold capturing said light transmitting member and said fluid transmitting member.

11. The flow cell of claim 1 wherein said light guiding member is a coating of an amorphous copolymer of perfluoro-2,2-dimethyl-1,3 dioxole and tetrafluoroethylene disposed on said inner surface of said chamber.

12. The flow cell of claim 1 wherein said light transmitting member is a transparent window.

13. The flow cell of claim 1 wherein said chamber is formed by a fused silica tube and said light guiding member is a coating of an amorphous copolymer of perfluoro-2,2-dimethyl-1,3 dioxole and tetrafluoroethylene disposed on an inner surface of said chamber.

14. A method for making a flow cell, comprising the steps of:
    forming a first and a second end interface each including a light transmitting member, a fluid transmitting member and an interface housing capturing each of said light transmitting member and said fluid transmitting member;
    forming a flow cell body by heating a plastic material to a temperature at which said plastic material is injection moldable,
    forming a through aperture with an inner surface, by disposing a light guiding member and fluid transmitting member in a flow cell interface molding tool to form an aperture in said flow cell body;
    injecting said plastic material into said flow cell end interface molding tool;
    cooling said plastic material; and
    securing said first end interface and said second end interface to form said flow cell body.

15. The method of claim 14 wherein said light transmitting member comprises an optical fiber and said fluid transmitting member comprises a capillary tube.

16. The flow cell of claim 14 wherein said light guiding member is a tubular member of an amorphous copolymer of perfluoro-2,2-dimethyl-1,3 dioxole and tetrafluoroethylene.

17. The method of claim 1 wherein said flow cell body is made from polyetheretherketone.

18. The method of claim 14 wherein said chamber is formed by a fused silica tube and said light guiding member is a coating of an amorphous copolymer of perfluoro-2,2-dimethyl-1,3 dioxole and tetrafluoroethylene disposed on an inner surface of said chamber.

19. The method of claim 14 wherein said light guiding member is a coating of an amorphous copolymer of perfluoro-2,2-dimethyl-1,3 dioxole and tetrafluoroethylene disposed on said inner surface of said chamber.

20. A System for analyzing a fluid sample comprising
    a radiation source;
    a sensing device for sensing radiation;
    a flow cell assembly including a flow cell for containing a fluid sample and for exposing the fluid sample to radiation from said radiation source for analysis, said flow cell comprising,
        a molded flow cell body having a through-aperture with an inner surface,
        a light guiding member disposed and fixed to said aperture inner surface by molding and having a wetted surface defining a chamber for receiving one or more fluids, said wetted surface comprised of a amorphous fluoropolymer having a refractive index less than the refractive index of said fluid sample to direct light impinging on said interior surface to reflect into said fluid sample;
        a first end interface and a second end interface, each of said first and second end interface comprising a light transmitting member; and inlet and outlet fluid transmitting members disposed in one of said flow cell body or first or second end surface.

21. The flow cell of claim 20 wherein said light guiding member is a tubular member of an amorphous copolymer of perfluoro-2,2-dimethyl-1,3 dioxole and tetrafluoroethylene.

22. The system for analyzing a fluid sample of claim 20 wherein said flow cell body is made from polyetheretherketone.

* * * * *